United States Patent
Doering et al.

(10) Patent No.: US 11,045,399 B2
(45) Date of Patent: *Jun. 29, 2021

(54) RESIDUE-MINIMIZED ANTIPERSPIRANT COMPOSITION WITH IMPROVED SKIN FEEL

(71) Applicant: Henkel AG & Co. KGaA, Duesseldorf (DE)

(72) Inventors: Thomas Doering, Dormagen (DE); Daniel Solich, Langenfeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 386 days.

This patent is subject to a terminal disclaimer.

(21) Appl. No.: 16/224,285

(22) Filed: Dec. 18, 2018

(65) Prior Publication Data

US 2019/0183753 A1 Jun. 20, 2019

(30) Foreign Application Priority Data

Dec. 19, 2017 (DE) .................... 10 2017 223 179.3

(51) Int. Cl.
| | |
|---|---|
| *A61K 8/26* | (2006.01) |
| *A61K 8/28* | (2006.01) |
| *A61K 8/73* | (2006.01) |
| *A61K 8/891* | (2006.01) |
| *A61K 8/04* | (2006.01) |
| *A61Q 15/00* | (2006.01) |
| *A61K 8/92* | (2006.01) |
| *A61K 8/37* | (2006.01) |
| *A61K 8/31* | (2006.01) |

(52) U.S. Cl.
CPC ................ *A61K 8/26* (2013.01); *A61K 8/044* (2013.01); *A61K 8/046* (2013.01); *A61K 8/28* (2013.01); *A61K 8/31* (2013.01); *A61K 8/37* (2013.01); *A61K 8/732* (2013.01); *A61K 8/891* (2013.01); *A61K 8/92* (2013.01); *A61Q 15/00* (2013.01); *A61K 2800/31* (2013.01); *A61K 2800/48* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 4,749,569 | A | 6/1988 | Gianino et al. |
| 4,777,034 | A | 10/1988 | Oliver et al. |
| 5,626,856 | A | 5/1997 | Berndt |
| 10,076,482 | B2 | 9/2018 | Aubrun et al. |
| 2003/0018577 | A1 | 1/2003 | Fukushima et al. |
| 2003/0185777 | A1 | 10/2003 | Banowski et al. |
| 2016/0000681 | A1 | 1/2016 | Aubrun et al. |
| 2018/0168947 | A1 | 6/2018 | Banowski et al. |

FOREIGN PATENT DOCUMENTS

| | | |
|---|---|---|
| DE | 19756454 C1 | 6/1999 |
| DE | 19962878 A1 | 6/2001 |
| FR | 3002140 A1 | 8/2014 |
| FR | 3046068 A1 | 6/2017 |
| FR | 3060365 A1 | 6/2018 |
| GB | 2096891 A | 10/1982 |
| GB | 2572070 A | 9/2019 |

*Primary Examiner* — Robert A Wax
*Assistant Examiner* — Randeep Singh
(74) *Attorney, Agent, or Firm* — Lorenz & Kopf, LLP

(57) ABSTRACT

The present disclosure relates to substantially anhydrous sweat-suppressing compositions which leave minimal residues on textiles and at the same time result in an improved skin feel after application, containing combinations of rice starch and cornstarch or maize amylopectin, volatile and non-volatile oils, and at least one sweat-suppressing active agent.

16 Claims, No Drawings

RESIDUE-MINIMIZED ANTIPERSPIRANT COMPOSITION WITH IMPROVED SKIN FEEL

CROSS-REFERENCE TO RELATED APPLICATION

This application claims priority to German Patent Application No. 10 2017 223 179.3, filed Dec. 19, 2017, which is incorporated herein by reference in its entirety.

TECHNICAL FIELD

The present disclosure relates to substantially anhydrous sweat-suppressing antiperspirant compositions which leave minimal residues on textiles and at the same time result in an improved skin feel after application, a non-therapeutic method for reducing and/or regulating sweat production and/or body odor, and the use of certain types of starch to improve skin feels while at the same time minimizing white residues on clothing following application of the antiperspirant composition.

BACKGROUND

Standard commercial sweat-suppressing compositions, also referred to in the following text as a antiperspirants, contain at least one water-soluble astringent, inorganic or organic salt of aluminum, zirconium or selected mixed aluminum-zirconium salts as the active sweat-suppressing (antiperspirant) agent. The active antiperspirant agents do not have any direct effect on the action of the sweat glands, but they minimize sweat secretion by constricting the excretory ducts. In this process, the Al salts inhibit sweat production on the treated skin surfaces by blocking the sweat gland ducts on the surface through Al-mucopolysaccharide deposits. Antiperspirant compositions are usually applied in the region of the armpits. When the composition begins to dry on the skin or the garment that his come into contact with the skin after the antiperspirant was applied, the sweat suppressing salt is often visible as a white residue. This also occurs, although to a much lesser degree, with compositions containing larger quantities of water, in which the sweat inhibiting salt is present in dissolved form. The white residues are perceived by the consumer as a very negative property of the product. Both water-soluble components, particularly 1.2-Propylene glycol for example, and oils, particularly ester oils such as isopropyl palmitate or alkyl benzoate, are known in the related art for masking aluminum salt residues of water-containing compositions. Masking agents of such kind moisten the sweat-suppressing salt and do not evaporate even after they are applied to the skin, as water and cyclomethicones do, for example. This causes the sweat-suppressing salt to dry significantly more slowly, and the appearance of visible residues is delayed.

However, the use of oils often results in an unpleasant, greasy skin feel for users, which is perceived as very unwelcome. This unpleasant skin feel becomes more pronounced with larger quantities of oils, which offer better masking of aluminum salt residues.

There is therefore a continuing need for antiperspirant compositions with good residue masking capability, less visible residues and non-greasy skin feel.

BRIEF SUMMARY

This disclosure provides a sweat suppressing composition for personal body care. This composition includes:

a) at least one sweat suppressing agent which is present in suspended, non-dissolved form and is selected from aluminum salts and aluminum-zirconium salts,
b) from about 0 to about 7% w/w free water,
c) at least one non-volatile oil that is liquid under normal conditions in a total quantity from about 28 to about 6% w/w,
d) at least one volatile oil that is liquid under normal conditions in a total quantity from about 5 to about 35% w/w,
e) from about 0.1 to about 5% w/w rice starch, and
f) from about 0.1 to about 5% w/w cornstarch or maize amylopectin,
wherein all percentages by weight relate to the weight of the composition in each case, disregarding any propellants present.

This disclosure also provides a non-therapeutic, cosmetic method for reducing and/or regulating sweat production and/or body odor, in which the aforementioned composition is applied in an effective quantity to the skin.

This disclosure further provides a sprayable antiperspirant including the aforementioned composition present in an aerosol container together with a compressed, gas-phase propellant.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

One problem to be solved with the present disclosure was to prepare antiperspirant compositions with high residue masking and reduced visible residues.

A further problem to be solved with the present disclosure was to prepare antiperspirant compositions with non-greasy skin feel.

Surprisingly, it was found that the stated problems may be solved with certain combinations of starch preparations, while the individual starch preparations had a considerably less pronounced effect, or none at all.

One object of the present disclosure is therefore a sweat suppressing composition for personal body care, containing
a) at least one sweat suppressing agent which is present in suspended, undissolved form and is selected from aluminum salts and aluminum-zirconium salts, preferably aluminum chlorohydrate,
b) from about 0 to about 7% w/w, preferably from about 0 to about 3% w/w, free water,
c) at least one non-volatile oil which is liquid under normal conditions in a total quantity from about 28 to about 61% w/w,
d) least one volatile oil which is liquid under normal conditions in a total quantity from about 5 to about 35% w/w,
e) from about 0.1 to about 5% w/w, preferably from about 0.2 to about 2% w/w, particularly preferably from about 0.4 to about 1% w/w rice starch,
f) from about 0.2 to about 5% w/w, preferably from about 0.2 to about 3% w/w, particularly preferably from about 0.4 to about 1.5% w/w cornstarch or maize amylopectin, preferably in hydrophobically modified form, wherein all weight percentage information is given relative to the weight of the respective composition, without consideration for any propellants present.

Within the meaning of the present application, "normal conditions" are a temperature of about 20° C. and a pressure of about 1013.25 mbar. Melting point data also refer to a pressure of about 1013.25 mbar.

Unless specified otherwise, all quantities indicated refer to the total weight of the sweat suppressing composition as contemplated herein. Any propellants adds are not considered for the purposes of the sweat suppressing composition as contemplated herein. Therefore, all quantities indicated refer to the total weight of the sweat suppressing composition without propellants, unless otherwise indicated.

Within the meaning of the present application, "free water" is water that is contained in the sweat suppressing composition but not in the form of water of crystallization, hydration water or similarly molecularly bonded water. The content of water of crystallization, hydration water or similarly molecularly bonded water which is contained in the constituents used, particularly in the sweat suppressing agents is not considered to be free water within the meaning of the present application. Free water is for example water which is added to the composition as contemplated herein as a solvent, as a gel activator or as a solvent component of other agents.

The compositions as contemplated herein contain from about 0 to about 7% w/w free water relative to their total weight. Antiperspirant compositions as contemplated herein preferably contain from about 0 to about 6% w/w free water, preferably from about 0 to about 5% w/w, particularly preferably from about 0 to about 4% w/w, most particularly preferably from about 0 to about 3% w/w free water relative to the total weight thereof. The compositions as contemplated herein are thus to be considered as substantially anhydrous.

Compositions as contemplated herein contain rice starch in a total quantity from about 0.2 to about 5% w/w, preferably form about 0.2 to about 2% w/w, particularly preferably from about 0.4 to about 1% w/w relative to the weight of the composition, preferably in the form of a powder treated with cationic surfactants, particularly preferably with cationic surfactant content from about 0.01 to about 0.3% w/w, most particularly preferably from about 0.2 to about 0.25% w/w relative to the weight of the rice starch. Preferred cationic surfactants are alkyltrimethylammonium chlorides, particularly preferably $C_{12}$-$C_{22}$-alkyltrimethylammonium chlorides, preferred is $C_{16}$-alkyltrimethylammonium chloride (cetrimonium chloride).

In compositions that are preferred as contemplated herein, amylose accounts for from about 10 to about 40% w/w, preferably from about 20 to about 30% w/w, particularly preferably from about 22 to about 28% w/w of the rice starch, and amylopectin accounts for from about 60 to about 90% w/w, preferably from about 70 to about 80% w/w, particularly preferably from about 72 to about 78% w/w relative to the weight of the rice starch.

Compositions as contemplated herein contain cornstarch or maize amylopectin in a total quantity from about 0.2 to about 5% w/w, preferably from about 0.2 to about 3% w/w, particularly preferably from about 0.4 to about 1.5% w/w relative to the weight of the composition, wherein the cornstarch or the maize amylopectin are preferably derivatized hydrophobically.

In particularly preferred compositions as contemplated herein, the cornstarch is present as a product of the complete or partial reaction of the hydrolyzate thereof with octenylsuccinic acid anhydride (=1-Octadecenylsuccinic acid anhydride) or with octenylsuccinic acid (=1-Octadecenylsuccinic acid).

Preferred compositions as contemplated herein contain the preferably hydrophobically derivatized cornstarch or the preferably hydrophobically derivatized maize amylopectin in the form of a capsule material for active agents, particularly deodorants, fragrances, perfume oils and/or skin cooling agents, but also other skin care agents such as vitamins or antioxidants.

In a further preferred embodiment, compositions as contemplated herein contain the preferably hydrophobically derivatized cornstarch or the preferably hydrophobically derivatized maize amylopectin as such or as such in powder form, that is to say not as a component of a capsule material.

The compositions as contemplated herein contain at least one sweat suppressing agent which is selected from aluminum salts and aluminum-zirconium salts. Preferred active antiperspirant agents are selected from the water-soluble astringent inorganic and organic salts of aluminum and zirconium and/or any mixtures of said salts.

As contemplated herein, solubility in water is understood to describe a solubility of least about 3% w/w at about 20° C., that is to say quantities of at least about 3 g of the antiperspirant agent can be dissolved in about 97 g of water at about 20° C. Preferably as contemplated herein, solubility in water is defined as a solubility of least about 5% w/w at about 20° C., that is to say quantities of at least about 5 g of the antiperspirant agent can be dissolved in about 95 g of water at about 20° C.

Particularly preferred antiperspirant agents are selected from aluminum chlorohydrate, particularly aluminum chlorohydrate with the general formula $[Al_2(OH)_5Cl.1\text{-}6H_2O]_n$, preferably $[Al_2(OH)_5Cl.2\text{-}3H_2O]_n$, which may exist in non-activated or activated (depolymerized) form, and aluminum chlorohydrate with the general formula $[Al_2(OH)_4Cl_2.1\text{-}6H_2O]_n$, preferably $[Al_2(OH)_4Cl_2.2\text{-}3H_2O]_n$, which may exist in non-activated or activated (depolymerized) form.

In compositions that are particularly preferred as contemplated herein, the sweat suppressing agent, preferably aluminum chlorohydrate, is present in the form of spherical particles, wherein particularly preferably from about 70 to about 95% w/w of the particles have a diameter larger than about 10 μm, from about 80 to about 100% w/w of the particles have a diameter up to about 75 μm and about 90 to about 100% w/w of the particles have a diameter up to about 125 μm, and most particularly preferably from about 75 to about 80% w/w of the particles have a diameter greater than about 10 μm, from about 90 to about 100% w/w of the particles have a diameter up to about 75 μm and from about 99 to about 100% w/w of the particles have a diameter up to about 125 μm, relative to the weight of the sweat suppressing agent in each case.

Also preferred are aluminum sesquichlorohydrate, aluminum dichlorohydrate, aluminum chlorohydrex-propylene glycol (PG) or aluminum chlorohydrex-polyethylene glycol (PEG), aluminum- or aluminum-zirconium glycol complexes, e.g., aluminum- or aluminum-zirconium propylene glycol complexes, aluminum sesquichlorohydrex-PG or aluminum sesquichlorohydrex-PEG, aluminum-PG-dichlorohydrex or aluminum-PEG-dichlorohydrex, aluminum hydroxide, further selected from the aluminum-zirconium chlorohydrates, such as aluminum zirconium trichlorohydrate, aluminum-zirconium tetrachlorohydrate, aluminum-zirconium pentachlorohydrate, aluminum-zirconium octachlorohydrate, the aluminum-zirconium-chlorohydrate-glycine complexes such as aluminum-zirconium trichlorohydrex glycine, aluminum-zirconium tetrachlorohydrex glycine, aluminum-zirconium pentachlorohydrex glycine, aluminum-zirconium octachlorohydrex glycine, potassium aluminum sulfate (KAl(SO$_4$)$_2$.12H$_2$O, alum), dehydrated alum (KAl(SO$_4$)$_2$ with from about zero to about 11 mol water of crystallization), sodium aluminum chlorohydroxylactate, aluminum hydrobromide, aluminum chloride, aluminum sulfate, aluminum lactate, sodium-aluminum-chlorohydroxylactate, zirconyl oxyhalides, particularly zirconyl oxychlorides, zirconyl hydroxyhalides, particularly zirconyl hydroxychlorides (zirconium chlorohydrate).

Antiperspirant agents that are particularly preferred as contemplated herein are selected from "activated" aluminum- and aluminum-zirconium salts, which are also described as "enhanced activity" antiperspirant agents. Agents of such kind are known in the related art and are also commercially available. Activated aluminum- and aluminum-zirconium salts are typically prepared by thermal treatment of a relatively dilute solution of the salt (e.g., about 10% w/w salt) to increase the HPLC-peak 4-to-peak 3 area ratio. The activated salt may then be dried, particularly spray-dried, to obtain a powder. Drum drying for example is suitable as well as spray drying.

Activated aluminum- and aluminum-zirconium salts typically have a HPLC-peak 4-to-peak 3 area ratio of at least about 0.4, preferably at least about 0.7, particularly preferably at least about 0.9, wherein at least about 70% of the aluminum is to be assigned to these peaks.

Activated aluminum- and aluminum-zirconium salts do not necessarily have to be used in the form of spray dried powder. Equally preferred sweat suppressing agents as contemplated herein are anhydrous solutions or solubilizates of an activated sweat suppressing aluminum- or aluminum-zirconium salt, which have been stabilized against the loss of activation against the rapid decay of the HPLC peak 4:peak 3 area ratio of the salt by the addition of an effective quantity of a polyvalent alcohol with from about 3 to about 6 carbon atoms and from about 3 to about 6 hydroxyl groups, preferably propylene glycol, sorbitol and pentaerythritol. For example, preferred compositions are those which contain, in percent by weight (USP): from about 18 to about 45% w/w of an activated aluminum- or aluminum-zirconium salt, from about 55 to about 82% w/w of at least one anhydrous polyvalent alcohol with from about 3 to about 6 carbon atoms and from about 3 to about 6 hydroxyl groups, preferably propylene glycol, butylene glycol, diethylene glycol, dipropylene glycol, glycerine, sorbitol and pentaerythritol, particularly preferably propylene glycol.

Particularly preferred are also complexes of activated sweat suppressing aluminum- or aluminum-zirconium salts with a polyvalent alcohol which contain from about 20 to about 50% w/w, particularly preferably from about 20 to about 42% w/w activated sweat suppressing aluminum- or aluminum-zirconium salt and from about 2 to about 16% w/w molecularly bound water, wherein the rest to about 100% w/w is at least one polyvalent alcohol with from about 3 to about 6 carbon atoms and from about 3 to about 6 hydroxyl groups. Propylene glycol, propylene glycol/sorbitol mixtures and propylene glycol/pentaerythritol mixtures are preferred alcohols of such kind.

Further preferred sweat suppressing agents are basic calcium-aluminum salt. These salts are prepared by reacting calcium carbonate with aluminum chlorhydroxide or aluminum chloride and aluminum powder or by adding calcium chloride dihydrate to aluminum chlorhydroxide.

Further preferred sweat suppressing agents are aluminum-zirconium complexes which have been buffered with salts of amino acids, particularly with alkaline and alkaline earth glycinates. Further preferred sweat suppressing agents are activated aluminum- or aluminum-zirconium salts, containing from about 5 to about 78% w/w (USP) of an activated sweat suppressing aluminum- or aluminum-zirconium salt, an amino acid or hydroxyalkanoic acid in such quantity as to create a weight ratio from about 2:1 to about 1:20 and preferably from about 1:1 to about 1:10 between (amino acid or hydroxyalkanoic acid) and (Al+Zr), and a water-soluble calcium salt in such quantity as to create a Ca:(Al+Zr) weight ratio from about 1:1 to about 1:28 and preferably from about 1:2 to about 1:25. Particularly preferred solid activated sweat suppressing salt compositions contain from about 48 to about 78% w/w (USP), preferably from about 66 to about 75% w/w of an activated aluminum- or aluminum-zirconium salt and from about 1 to about 16% w/w, preferably from about 4 to about 13% w/w of molecularly bound water (hydration water), and a sufficient quantity of water-soluble calcium salt so that the Ca:(Al+Zr) weight ratio is from about 1:1 to about 1:28, preferably from about 1:2 to about 1:25, and a sufficient quantity of amino acid so that the weight ratio between the amino acid and (Al+Zr) is from about 2:1 to about 1:20, preferably from about 1:1 to about 1:10.

Further particularly preferred solid sweat suppressing activated salt compositions contain from about 48 to about 78% w/w (USP), preferably from about 66 to about 75% w/w of an activated aluminum- or aluminum-zirconium salt and from about 1 to about 16% w/w, preferably from about 4 to about 13% w/w of molecularly bound water (hydration water), and a sufficient quantity of water-soluble calcium salt so that the Ca:(Al+Zr) weight ratio is from about 1:1 to about 1:28, preferably from about 1:2 to about 1:25, and a sufficient quantity of glycine so that the weight ratio of glycine to (Al+Zr) is from about 2:1 to about 1:20, preferably from about 1:1 to about 1:10.

Further particularly preferred solid sweat suppressing activated compositions contain from about 48 to about 78% w/w (USP), preferably from about 66 to about 75% w/w of an activated aluminum- or aluminum-zirconium salt and from about 1 to about 16% w/w, preferably from about 4 to about 13% w/w molecularly bound water, and a quantity of water-soluble calcium salt such that the Ca:(Al+Zr) weight ratio is from about 1:1 to about 1:28, preferably from about 1:2 to about 1:25, and a quantity of hydroxyalkanoic acid such that the weight ratio of hydroxyalkanoic acid to (Al+Zr) is from about 2:1 to about 1:20, preferably from about 1:1 to about 1:10.

Preferred water-soluble calcium salts for stabilizing the sweat suppressing salts are selected from calcium chloride, calcium bromide, calcium nitrate, calcium citrate, calcium formate, calcium acetate, calcium gluconate, calcium ascorbate, calcium lactate, calcium glycinate, calcium carbonate, calcium sulfate, calcium hydroxide, and mixtures thereof.

Preferred amino acids for stabilizing the sweat suppressing salts are selected from glycine, alanine, leucine, isoleucine, β-alanine, valine, cysteine, serine, tryptophan, phenylalanine, methionine, β-amino-n-butanoic acid and γ-amino-n-butanoic acid and the salts thereof, each in the d-form, the l-form and the dl-form; glycine is particularly preferred.

Preferred hydroxyalkanoic acids for stabilizing the sweat suppressing salts are selected from glycolic acid and lactic acid.

Further preferred sweat suppressing agents are activated aluminum- or aluminum-zirconium salts which contain from about 5 to about 78% w/w (USP) of an activated sweat suppressing aluminum- or aluminum-zirconium salt, an amino acid or hydroxyalkanoic acid in a quantity such as to obtain a weight ratio between (amino acid or hydroxyalkanoic acid) and (Al+Zr) between from about 2:1 to about 1:20 and preferably from about 1:1 to about 1:10, and a water-soluble strontium salt in a quantity such as to obtain a Sr:(Al+Zr) weight ratio from about 1:1 to about 1:28 and preferably from about 1:2 to about 1:25.

Particularly preferred solid sweat suppressing activated salt compositions contain from about 48 to about 78% w/w (USP), preferably from about 66 to about 75% w/w of an activated aluminum- or aluminum-zirconium salt and
from about 1 to about 16% w/w, preferably from about 4 to about 13% w/w molecularly bound water, and a quantity of water-soluble strontium salt such that the Sr:(Al+Zr) weight ratio is from about 1:1 to about 1:28, preferably from about 1:2 to about 1:25, and a quantity of amino acid such that the weight ratio of amino acid to (Al+Zr) is from about 2:1 to about 1:20, preferably from about 1:1 to about 1:10.

Further particularly preferred solid sweat suppressing activated salt compositions contain
from about 48 to about 78% w/w (USP), preferably from about 66 to about 75% w/w of an aluminum- or aluminum-zirconium salt and
from about 1 to about 16% w/w, preferably from about 4 to about 13% w/w molecularly bound water, and a quantity of water-soluble strontium salt such that the Sr:(Al+Zr) weight ratio is from about 1:1 to about 1:28, preferably from about 1:2 to about 1:25, and a quantity of glycine such that the weight ratio of glycine to (Al+Zr) is from about 2:1 to about 1:20, preferably from about 1:1 to about 1:10.

Further particularly preferred solid sweat suppressing activated salt compositions contain
from about 48 to about 78% w/w (USP), preferably from about 66 to about 75% w/w of an aluminum- or aluminum-zirconium salt and
from about 1 to about 16% w/w, preferably from about 4 to about 13% w/w molecularly bound water, and a quantity of water-soluble strontium salt such that the Sr:(Al+Zr) weight ratio is from about 1:1 to about 1:28, preferably from about 1:2 to about 1:25, and a quantity of hydroxyalkanoic acid such that the weight ratio of hydroxyalkanoic acid to (Al+Zr) is from about 2:1 to about 1:20, preferably from about 1:1 to about 1:10.

Further preferred activated aluminum salts are those having the general formula $Al_2(OH)_{6-a}Xa$, in which X is Cl, Br, I or $NO_3$ and "a" is a value from about 0.3 to about 5, preferably from about 0.8 to about 2.5 and particularly preferably from about 1 to about 2, so that the molar ratio Al:X is from about 0.9:1 to about 2.2:1, as are disclosed in U.S. Pat. No. 6,074,632 for example. These salts generally contain a small quantity of associatively bound hydration water, typically from about 1 to about 6 mol water per mol salt. Particularly preferred is aluminum chlorohydrate (i.e. X is Cl in the formula cited previously) and specifically 5/6-basic aluminum chlorohydrate, in which "a" is equal to about 1, so that the molar ratio of aluminum to chlorine is from about 1.9:1 to about 2.2:1. Zirconium-free aluminum sesquichlorohydrates which are particularly preferred as contemplated herein have a molar metal-to-chloride ratio from about 1.5:1 to about 1.8:1.

Preferred activated aluminum-zirconium salts are those which represent mixtures or complexes of the aforementioned aluminum salts with zirconium salts having formula $ZrO(OH)_{2-pb}Y_b$, in which Y is Cl, Br, I, $NO_3$ or $SO_4$, b is a rational number from about 0.8 to about 2 and p is the valence of Y, as are disclosed in U.S. Pat. No. 6,074,632 for example. The zirconium salts typically also contain a small quantity of associatively bound hydration water, typically from about 1 to about 7 mol water per mol salt. The zirconium salt is preferably zirconyl hydroxychloride with formula $ZrO(OH)_{2-b}Cl_b$, in which b is a rational number from about 0.8 to about 2, preferably from about 1.0 to about 1.9. Preferred aluminum-zirconium salts have an Al:Zr molar ratio from about 2 to about 10 and a metal:(X+Y) ratio from about 0.73 to about 2.1, preferably from about 0.9 to about 1.5. A particularly preferred salt is aluminum-zirconium chlorohydrate (i.e. X and Y are Cl), which has an Al:Zr ratio from about 2 to about 10 and a molar metal:Cl ratio from about 0.9 to about 2.1. The term aluminum-zirconium chlorohydrate includes the tri-, tetra-, penta- and octachlorohydrate forms.

Preferred zirconium salts as contemplated herein have the general formula $ZrO(OH)_{2-a}Cl_a \cdot x\, H_2O$ with a=from about 1.5 to about 1.87; x=from about 1 to about 7, wherein a and x are rational numbers.

Preferred aluminum-zirconium salts have a molar metal-to-chloride ratio from about 0.9 to about 1.3, preferably from about 0.9 to about 1.2, particularly preferably from about 0.9 to about 1.0.

Preferred aluminum-zirconium chlorohydrates generally have the empirical formula $Al_nZr(OH)_{[3n+4-m(n+1)]}(Cl)_{[m(n+1)]}$ with n=from about 2.0 to about 10.0, preferably from about 3.0 to about 8.0, m=from about 0.77 to about 1.21 (corresponding to a molar metal (Al+Zr)-to-chloride ratio from about 1.3 to about 0.9), preferably m=from about 0.91 to about 1.21 (corresponding to M:Cl=from about 1.2 to about 0.9), and particularly preferably m=from about 1.00 to about 1.21 (corresponding to M:Cl=from about 1.0 to about 0.9), also very preferably m=from about 1.02 to about 1.21 (corresponding to M:Cl=from about 0.98 to about 0.9) and most particularly preferably m=from about 1.04 to about 1.21 (corresponding to M:Cl=from about 0.96 to about 0.9).

A small amount of associatively bound hydration water is present in these salts, typically from about 1 to about 6 mol water per mol salt, corresponding to from about 1 to about 16% w/w, preferably from about 4 to about 13% w/w hydration water.

The preferred aluminum-zirconium chlorohydrates are usually associated with an amino acid to prevent polymerization of the zirconium species during production. Preferred stabilizing amino acids are selected from glycine, alanine, leucine, isoleucine, β-alanine, cysteine, valine, serine, tryptophan, phenylalanine, methionine, β-amino-n-butanoic acid and γ-amino-n-butanoic acid and the salts thereof, each in the d-form, the l-form and the dl-form; glycine is particularly preferred. The amino acid is contained in the salt in a quantity from about 1 to about 3 mol, preferably from about 1.3 to about 1.8 mol, per mole zirconium in each case.

Preferred sweat suppressing salts are aluminum-zirconium tetrachlorohydrate (Al:Zr=from about 2 to about 6; M:Cl=from about 0.9 to about 1.3), particularly salts with a molar metal-to-chloride ratio from about 0.9 to about 1.2, preferably from about 0.9 to about 1.0.

Also preferred as contemplated herein are aluminum-zirconium chlorohydrate-glycine salts, which are stabilized with betaine $((CH_3)_3N^+$—$CH_2$—$COO^-)$. The overall molar ratio between (betaine+glycine) and Zr in particularly preferred compounds of this kind is (from about 0.1 to about 3.0): 1, preferably (from about 0.7 to about 1.5): 1, and the molar ratio between betaine and glycine is at least about 0.001:1. In a particularly preferred embodiment as contemplated herein, an "activated salt" is contained as a particularly effective antiperspirant salt, in particular one with a high HPLC peak 5 aluminum content, particularly with a peak 5 area of at least about 33%, particularly preferably at least about 45%, relative to the total area below peaks from about 2 to about 5, measured with HPLC of a about 10% w/w aqueous solution of the active ingredient under conditions in which the aluminum species are broken down into at least about 4 consecutive peaks (denoted as peaks from about 2 to about 5).

Activated "E$^5$AZCH" salts whose HPLC peak 4-to-peak 3 area ratio is at least about 0.4, preferably at least about 0.7, particularly preferably at least about 0.9 are also particularly preferred.

Further particularly preferred antiperspirant agents are those aluminum-zirconium salts with a high HPLC peak 5 aluminum contents which are additionally stabilized with a water-soluble strontium salt and/or with a water-soluble calcium salt.

Particularly preferred compositions as contemplated herein are exemplified in that the at least one antiperspirant agent is present in the composition in a total quantity from about 5 to about 40% w/w, preferably from about 10 to about 35% w/w, particularly preferably from about 15 to about 28% w/w and most particularly preferably from about 23 to about 27% w/w relative to the total weight of the active substance with no water of crystallization (USP), disregarding any propellants present.

The compositions as contemplated herein contain at least one non-volatile oil which is liquid under normal in a total quantity from about 28 to about 61% w/w, preferably from about 30 to about 50% w/w, particularly preferably from about 32 to about 45% w/w, most particularly preferably from about 35 to about 38% w/w, and at least one volatile oil which is liquid under normal in a total quantity from about 5 to about 35% w/w, preferably from about 10 to about 30% w/w, particularly preferably from about 15 to about 25% w/w, most particularly preferably from about 20 to about 22% w/w as further ingredients.

Non-volatile oils are understood to be those oils which exhibit a vapor pressure lower than about 2.66 Pa (about 0.02 mm Hg) at about 20° C. and under ambient pressure of about 1013 hPa. Volatile oils are understood to be those oils which exhibit a vapor pressure of from about 2.66 Pa to about 40000 Pa (from about 0.02 mm to about 300 mm Hg), preferably from about 12 to about 12000 Pa (from about 0.2 to about 90 mm Hg), particularly preferably from about 13 to about 8000 Pa, most particularly preferably from about 30 to about 3000 Pa, still more preferably from about 100 to about 400 Pa at about 20° C. and under ambient pressure of about 1013 hPa.

Compositions as contemplated herein preferably contain esters of linear or branched saturated or unsaturated fatty alcohols having from about 2 to about 30 carbon atoms with linear or branched saturated or unsaturated fatty acids with from about 2 to about 30 carbon atoms, which may or may not be hydroxylated as the at least one non-volatile oil. Most particularly preferred among these are isopropyl myristate, isopropyl palmitate, isopropyl stearate, 2-Ethylhexyl palmitate and 2-Ethylhexyl stearate. Also preferred are 2-Hexyldecyl stearate, 2-Hexyldecyl laurate, isononyl isononanoate, isooctyl stearate, isononyl stearate, isocetyl stearate, isononyl isononanoate, isotridecyl isononanoate, cetearyl isononanoate, 2-Ethylhexyl laurate, 2-Ethylhexyl isostearate, 2-Ethylhexyl cocoate, 2-Octyldodecyl palmitate, butyloctanoic acid-2-butyloctanoate, diisotridecyl acetate, n-Hexyl laurate, n-Decyl oleate, oleyl oleate, oleyl erucate, erucyl oleate and erucyl erucate and mixtures of said esters.

Further preferred non-volatile oils as contemplated herein are selected from the mono- and multi-esters of lactic acid, citric acid, tartaric acid or adipic acid with a monovalent alcohol having from about 2 to about 9 carbon atoms. A particularly preferred ester of this kind is triethyl citrate.

Non-volatile oils which are most particularly preferred as contemplated herein are selected from isopropyl myristate, isopropyl palmitate, isopropyl stearate, 2-Ethylhexyl palmitate, 2-Ethylhexyl stearate and triethyl citrate, and mixtures of said esters.

Further non-volatile oils which are preferred as contemplated herein are selected from the dicarboxylic acid esters of linear or branched $C_2$-$C_{10}$-alkanols, particularly diisopropyl adipate, di-n-butyl adipate, di-(2-ethylhexyl)adipate, dioctyl adipate, diethyl-/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl)-succinate and mixtures of said esters.

Further non-volatile oils which are preferred as contemplated herein are selected from the benzoic acid esters of linear or branched $C_{8-22}$-alkanols. Preferred alkyl benzoates are dodecyl benzoate, tridecyl benzoate, tetradecyl benzoate, pentadecyl benzoate, hexadecyl benzoate, octadecyl benzoate, 2-Methyl-heptadecyl benzoate, octyldodecyl benzoate. Particularly preferred are benzoic acid-C12-C15-alkyl esters, which are available for example as the commercial product Finsolv® TN, benzoic acid isostearyl esters, 2-Ethylhexyl benzoate and benzoic acid-2-octyldocecyl esters, wherein benzoic acid-C12-C15-alkyl esters are most particularly preferred.

Further non-volatile oils which are preferred as contemplated herein are selected from the mono- and multi-esters of lactic acid, citric acid, tartaric acid or adipic acid with mono-, bi-, tri- or tetravalent alcohol having from about 2 to about 9 carbon atoms.

In principle, triglyceride oils of linear or branched, saturated or unsaturated, optionally hydroxylated $C_{8-30}$-fatty acids, particularly natural oils such as soybean oil, cottonseed oil, sunflower oil, palm oil, palm kernel oil, linseed oil, almond oil, castor oil, corn oil, rapeseed oil, olive oil, sesame oil, safflower oil, wheatgerm oil, peach kernel oil and liquid components of coconut oil and the like, but also synthetic triglyceride oil, particularly capric/caprylic triglycerides, e.g., the commercial products Myritol® 318 or Myritol® 331 (BASF) with unbranched fatty acid radicals and glyceryl triisostearin with branched fatty acid radicals are also suitable for use as non-volatile oils, but they are less preferred due to their less favorable residue behavior. Triglyceride oils of such kind should preferably only be included in a total quantity from about 0 to about 1% w/w, particularly preferably from about 0 to about 0.5% w/w, in each case relative to the weight of the composition, disregarding any propellants present.

Further non-volatile oils which are preferred as contemplated herein are selected from the symmetrical, unsymmetrical or cyclic esters of carbonic acid with fatty alcohols, e.g., dicaprylyl carbonate (Cetiol® CC), di-n-octyl carbonate, di-n-dodecyl carbonate, di-(2-ethylhexyl)carbonate or the ester according to the teaching of DE 19756454 A.

Further preferred non-volatile oils are selected from non-volatile silicone oils. Preferred non-volatile silicone oils are selected from linear polydimethyl siloxanes with kinematic viscosities (about 25° C.) in the range from about 5 to about 350 cSt, preferably in the range from about 5 to about 100 cSt, particularly preferably in the range from about 10 to about 50 cSt.

Compositions as contemplated herein preferably contain a volatile silicone oil as the at least one volatile oil. Preferred volatile silicone oils are selected from dialkyl- and alkylaryl siloxanes which exhibit a vapor pressure less than about 2.66

Pa (about 0.02 mm Hg) at about 20° C. and under ambient pressure of about 1013 hPa, such as for example octamethyl cyclotetrasiloxane, decamethyl cyclopentasiloxane, dodecamethyl cyclohexasiloxane, dimethyl polysiloxane, low-molecular phenyl trimethicone and methylphenyl polysiloxane, but also hexamethyl disiloxane, octamethyl trisiloxane and decamethyl tetrasiloxane. Particularly preferred are volatile silicone oils which are cyclic, such as octamethyl cyclotetrasiloxane, decamethyl cyclopentasiloxane and dodecamethyl cyclohexasiloxane and mixtures thereof, such as are contained for example in the commercial products DC 244, 245, 344 and 345 from Dow Corning (vapor pressure at about 20° C. approx. 13 to about 15 Pa).

Also particularly preferred are volatile linear silicone oils having from about 2 to about 10 siloxane units, particularly hexamethyl disiloxane ($L_2$), octamethyl trisiloxane ($L_3$), decamethyl tetrasiloxane ($L_4$) and any mixtures of two or three of $L_2$, $L_3$ and/or $L_4$, preferably such mixtures as are contained for example in the commercial products DC 2-1184, Dow Corning® 200 (about 0.65 cSt) and Dow Corning® 200 (about 1.5 cSt) from Dow Corning. A further preferred volatile silicone oil is a low-molecular phenyl trimethicone exhibiting a vapor pressure of about 2000 Pa at about 20° C., such as is available from GE Bayer Silicones/Momentive for example under the name Baysilone Fluid PD 5.

Volatile silicone oils are ideally suitable as carrier oils for antiperspirant composition as contemplated herein, since they lend a pleasant feel to the skin and cause low textile soiling.

Antiperspirant compositions as contemplated herein are therefore exemplified in that the at least one volatile silicone oil is selected from octamethyl cyclotetrasiloxane, decamethyl cyclopentasiloxane, dodecamethyl cyclohexasiloxane, hexamethyl disiloxane, octamethyl trisiloxane and decamethyl tetrasiloxane and mixtures thereof, particularly decamethyl cyclopentasiloxane, mixtures of decamethyl cyclopentasiloxane and dodecamethyl cyclohexasiloxane and mixtures of hexamethyl disiloxane, octamethyl trisiloxane and decamethyl tetrasiloxane, particularly preferably selected from decamethyl cyclopentasiloxane.

Further antiperspirant compositions as contemplated herein are exemplified by a total content of at least one volatile silicone oil from about 5 to about 35% w/w, preferably from about 10 to about 30% w/w, particularly preferably from about 15 to about 25% w/w, most particularly preferably from about 20 to about 22% w/w, wherein all values for percentage by weight refer to the weight of the respective antiperspirant composition, disregarding any propellants present.

Particularly preferred composition as contemplated herein are exemplified in that that they contain cyclopentasiloxane in a quantity from about 5 to about 35% w/w, preferably from about 10 to about 30% w/w, particularly preferably from about 15 to about 25% w/w, most particularly preferably from about 20 to about 22% w/w as a volatile oil component, wherein all values for percentage by weight refer to the weight of the respective antiperspirant composition, disregarding any propellants present.

Besides the at least one volatile silicone oil, preferred compositions as contemplated herein contain from about 7 to about 20% w/w, preferably from about 8 to about 17% w/w, particularly preferably from about 11 to about 16% w/w, most particularly preferably from about 12 to about 13% w/w PPG-14 butyl ether, wherein all values for percentage by weight refer to the weight of the respective antiperspirant composition, disregarding any propellants present.

Further preferred compositions as contemplated herein contain volatile non-silicone oils as volatile oils. Preferred volatile non-silicone oils are selected from $C_8$-$C_{16}$-isoparaffins, particularly from isodecane, isoundecane, isododecane, isotridecane, isotetradecane, isopentadecane, and isohexadecane, and mixtures thereof.

Further preferred compositions as contemplated herein contain mixtures of volatile silicone oils and volatile non-silicone oils as volatile oils.

Besides the aforementioned indispensable oil mixtures, at least one additional natural or synthetic hydrocarbon oil selected from paraffin oils, $C_8$-$C_{30}$-isoparaffins, particularly isoeicosane, polyisobutene or polydecene, which are available commercially for example the trade name Emery® 3004, 3006, 3010 or under the trade name Ethylflo® from Albemarle, or Nexbase® 2004G from Nestle, and 1.3-Di-(2-ethylhexyl)-cyclohexane (available e.g., under the trade name Cetiol® S from BASF) may be contained, preferably in a total quantity from about 0.2 to about 7% w/w, preferably from about 0.2 to about 5% w/w, particularly preferably from about 0.5 to about 2% w/w relative to the total composition in each case, wherein any propellants present are disregarded.

Further additional oils preferred as contemplated herein are selected from branched saturated or unsaturated fatty alcohols having from about 6 to about-30 carbon atoms. These alcohols are often also called Guerbet alcohols, because they can be obtained according to the Guerbet reaction. Preferred alcohol oils are 2-Hexyldecanol, octyldodecanol (Eutanol® G) and 2-Ethylhexyl alcohol.

Most particularly preferred compositions as contemplated herein contain a mixture of isopropyl myristate, 2-Ethylhexyl palmitate and polydimethyl siloxane with a viscosity of about 5 cSt as the at least one non-volatile oil (c) which is liquid under normal conditions, and decamethyl cyclopentasiloxane as the at least one volatile oil (d) which is liquid under normal conditions.

Fragrances and aromatic substances are not included among the indispensable oils as contemplated herein.

The definition of an aromatic substance within the meaning of the present application corresponds to the definition conventionally accepted among persons skilled in the art, as may be found in RÖMPP's Chemistry Lexicon, issue of December 2007. Accordingly, an aromatic substance is a chemical compound having odor and/or taste which activates the receptors in the hair cells of the olfactory system (adequate stimulus). The physical and chemical properties necessary for this are a low molar mass of not more than 300 g/mol, a high vapor pressure, minimal solubility in water but high solubility in lipids and weak polarity and the presence of at least one osmophoric group in the molecule. For the purposes of distinction between volatile, low-molecular substances which usually and also within the meaning of the present application are not considered and used as aromatic substances, but predominantly as solvents, such as ethanol, propanol, isopropanol and acetone, and aromatic substances as contemplated herein, aromatic substances as contemplated herein have a molar mass from about 74 to about 300 g/mol, contain at least one osmophoric group in the molecule, and have a smell and/or taste, that is to say they excite the receptors in the hair cells of the olfactory system. Examples of fragrances and aromatic substance compounds of the ester type are benzyl acetate, phenoxyethyl isobutyrate, p-tert.-Butylcyclohexyl acetate, linalyl acetate, dimethyl benzyl carbinyl acetate (DMBCA), phenylethyl acetate, benzyl acetate, ethylmethyl phenyl glycinate, allylcyclohexyl propionate, styrallyl propionate, benzyl salicylate, cyclohexyl salicylate, floramate, melusate and jasmecyclate, examples of fragrances and aromatic substance compounds of the ether type are benzyl ethyl ether and ambroxan, examples of fragrances and aromatic substance compounds of the aldehyde type are the linear alkanals having from about 8 to about 18 C atoms, citral, citronellal, citronellyl oxyacetaldehyde, cyclamen aldehyde, lilial and bourgeonal, examples of fragrance and aromatic substance compounds of the ketone type are jonone, alpha-isomethyl-ionone and methylcedryl ketone, examples of Examples of fragrances and aromatic substance compounds of the alcohol type are anethol, citronellol, eugenol, geraniol, linalool, phenylethyl alcohol and terpineol, examples of fragrances and aromatic substance compounds of the terpene type are limonene and pinene. Examples of fragrances and aromatic substance compounds are pine, citrus, jasmine, patchouli, rose, ylang-ylang oil, clary sage oil, chamomile oil, clove oil, mint oil, cinnamon leaf oil, lime blossom oil, juniper berry oil, vetiver oil, olibanum oil, *galbanum* oil, labdanum oil, orange blossom oil, neroli oil, orange peel oil and sandalwood oil, also the essential oils such as *angelica* root oil, aniseed oil, *arnica* blossom oil, basil oil, bay oil, bergamot oil, champaca blossom oil, silver fir oil, silver fir cone oil, elemi oil, *eucalyptus* oil, fennel oil, spruce needle oil, geranium oil, ginger grass oil, guaiacum wood oil, gurjun balsam oil, helichrysum oil, ho oil, ginger oil, iris oil, cajeput oil, calamus oil, chamomile oil, camphor oil, *cananga* oil, cardamom oil, *cassia* oil, pine needle oil, copaiba balsam oil, coriander oil, spearmint oil, caraway oil, cumin oil, lavender oil, lemongrass oil, lime oil, mandarin oil, sweet balm, musk mallow seed oil, myrrh oil, clove oil, niaouli oil, orange oil, oregano oil, palmarosa oil, patchouli oil, Peru balsam oil, petitgrain oil, pepper oil, peppermint oil, pimento oil, pine oil, rose oil, rosemary oil, sandalwood oil, celery oil, spike lavender oil, anise-burnet saxifrage oil, turpentine oil, *thuja* oil, thyme oil, *verbena*, oil, juniper berry oil, wormwood oil, wintergreen oil, hyssop oil, cinnamon oil, citronella oil, lemon peel oil and cypress oil. Further fragrance and aromatic substance compounds are ambrettolide, alpha-amyl cinnamic aldehyde, anethole, anisaldehyde, anise alcohol, anisole, methyl anthranilate, acetophenone, benzyl acetone, benzaldehyde, ethyl benzoate, benzophenone, benzyl alcohol, benzyl acetate, benzyl benzoate, benzyl formate, benzyl valerianate, borneol, bornyl acetate, alpha-bromostyrene, n-decylaldehyde, n-dodecylaldehyde, eugenol, eugenol methyl ether, eucalyptol, farnesol, fenchone, fenchyl acetate, geranyl acetate, geranyl formate, heliotropin, heptincarboxylic acid methyl ester, heptaldehyde, hydroquinone dimethyl ether, hydroxycinnamaldehyde, hydroxycinnamyl alcohol, indole, iron, isoeugenol, isoeugenol methyl ether, isosafrole, jasmone, camphor, carvacrol, carvone, p-cresol methyl ether, coumarin, p-Methoxyacetophenone, methyl n-amyl ketone, methylanthranil-acid-methylester, p-methylacetophenone, methyl chavicol, p-methylquinoline, methyl-β-naphthyl ketone, methyl-n-nonylacetaldehyde, methyl-n-nonyl ketone, muscone, β-Naphtholethylether, β-Naphtholmethylether, nerol, nitrobenzene, n-nonyl aldehyde, nonyl alcohol, n-octylaldehyde, p-oxy-acetophenone, pentadecanolide, beta-phenylethyl alcohol, phenyl acetaldehyde dimethylacetaate, phenylacetic acid, pulegone, safrole, salicylic acid isoamylester, salicylic acid methylester, salicylic acid hexylester, salicylic acid cyclohexylester, santalol, skatole, terpineol, thyme, thymol, γ-Undecalactone, vanillin, veratraldehyde, cinnamic aldehyde, cinnamic alcohol, cinnamic acid, cinnamic acid ethyl ester and cinnamic acid benzyl ester.

Further (more readily volatile) aromatic substances are alkylisothiocyanates (alkyl mustard oils), butanedione, limonene, linalool, linayl acetate and propionate, menthol, menthone, methyl-n-heptenone, phellandrene, phenyl acetaldehyde, terpinyl acetate, citral and citronella.

Preferably, mixtures of various fragrances as used, and these produce a corresponding scent together.

Suitable perfume oils may also contain natural aromatic substance mixtures, such as may be obtained from plant or animal sources, e.g., pine, citrus, jasmine, rose, lily or ylang-ylang oil. Less volatile essential oils which are usually used as aroma components are also suitable for use as perfume oils, e.g., sage oil, chamomile oil, sweet balm, mint oil, cinnamon leaf oil, lime blossom oil, juniper berry oil, vetiver oil, oliban oil, *galbanum* oil, laudanum oil, clove oil, isoeugenol, thyme oil, bergamot oil, geranium oil and rose oil.

Compositions that are preferred as contemplated herein are exemplified in that at least one fragrance substance is contained in a total quantity from about 0.1 to about 15% w/w, preferably from about 0.5 to about 10% w/w, particularly preferably from about 1 to about 8% w/w, most particularly preferably from about 2 to about 7% w/w, still more particularly preferably from about 3 to about 6% w/w, relative to the total weight of the propellant-free composition in each case.

Further compositions that are preferred as contemplated herein are exemplified by a content of at least one "skin cooling agent". Within the meaning of the present disclosure, skin cooling agents are understood to be agents which produce a pleasant soothing effect upon application to the skin due to a surface numbing action and stimulation of the cold-sensitive receptors in cases of migraine and the like, although the treated areas of the skin actually retain their normal or elevated temperature. Compound that are to be considered skin cooling agents as contemplated herein are those which, like 1-menthol, stimulate the thermoreceptors in the skin and the mucous membranes so that a cool sensory impression is created. The CMR-1 receptor ("cold- and menthol-sensitive receptor") in particular, a member of the TRP channel family, is stimulated by the cooling agents, producing a cooling sensation.

Preferred skin cooling agents are menthol, isopulegol and menthol derivatives, e.g., menthyl lactate, menthyl pyrrolidone carboxylic acid, methylmethyl ether, menthoxypropanediol, menthone glycerin acetal (9-Methyl-6-(1-methylethyl)-1.4-dioxaspiro(4.5)decane-2-methanol), monomenthyl succinate and 2-Hydroxymethyl-3.5.5-trimethylcyclohexanol. Particularly preferred skin cooling agents are menthol, isopulegol, menthyl lactate, menthoxypropanediol and menthyl pyrrolidone carboxylic acid. Preferred compositions as contemplated herein contain at least one skin cooling agent in a total quantity from about 0.01 to about 1% w/w, preferably from about 0.02 to about 0.5% w/w and particularly preferably from about 0.05 to about 0.2% w/w, relative in each case to the total weight of the (propellant-free) composition.

Preferred compositions as contemplated herein are exemplified in that at least one encapsulated agent is contained. The agents may advantageously be encapsulated are particularly deodorants (see below), fragrances, perfume oils and/or skin cooling agents, but they may also be other skin care agents such as vitamins, antioxidants etc.

The compositions as contemplated herein may also contain deodorant agents. Antimicrobial, antibacterial or germ-inhibiting substances, antioxidants or odor absorbers (e.g., zinc ricinoleate) may be used as deodorant agents. Suitable antimicrobial, antibacterial or germ-inhibiting substances are in particular organohalogen compounds and halides, quaternary ammonium compounds, a series of plant extracts and zinc compounds. Preferred are halogenated phenol derivatives such as hexachlorophene or Irgasan DP 300 (Triclosan, 2,4,4'-Trichloro-2'-hydroxydiphenylether), 3,4, 4'-Trichlorocarbanilide, chlorohexidine (1,2'-Hexamethylene-bis-[5-(4-chlorphenyl)]-biguanide), chlorohexidine gluconate, benzalkonium halides and cetylpyridinium chloride. Sodium bicarbonate, sodium phenolsulfonate and zinc phenolsulfonate as well as the components of the lime blossom oils for example are also usable. Substances with weaker antimicrobial effect which however are specifically effective against the gram-positive microbes responsible for the decomposition of sweat may also be used as deodorant agents. Benzyl alcohol may also be used as a deodorant agent. Further deodorants with antibacterial action as lantibiotics, glycoglycerolipids, sphingolipids (ceramides), sterines and other agents that inhibit the adhesion of bacteria to the skin, e.g., glycosidases, lipases, proteases, carbohydrates, di- and oligosaccharide fatty acid esters and alkylated mono- and oligosaccharides. Preferred deodorant agents are long-chain diols, e.g., 1.2-Alkane-($C_5$-$C_{18}$)-diols, glycerine mono($C_8$-$C_{18}$)-fatty acid esters or, particularly preferably, glycerine mono-($C_6$-$C_{16}$)-alkyl ethers, particularly 2-Ethylhexyl glycerine ethers, which are very well tolerated by the skin and mucous membrane and highly effective against Corynebacteria, as well as phenoxyethanol, phenoxyisopropanol (3-Phenoxypropane-2-ol), anise alcohol, 2-Methyl-5-phenyl-pentan-1-ol, 1.2-Dimethyl-3-phenylpropan-1-ol, benzyl alcohol, 2-Phenylethan-1-ol, 3-Phenylpropan-1-ol, 4-Phenylbutan-1-ol, 5-Phenylpentan-1-ol, 2-Benzylheptan-1-ol, 2.2-Dimethyl-3-phenylpropan-1-ol, 2.2-Dimethyl-3-(3'-methylphenyl)-propan-1-ol, 2-Ethyl-3-phenylpropan-1-ol, 2-Ethyl-3-(3'-methylphenyl)-propan-1-ol, 3-(3'-Chlorophenyl)-2-ethylpropan-1-ol, 3-(2'-Chlorophenyl)-2-ethylpropan-1-ol, 3-(4'-Chlorophenyl)-2-ethylpropan-1-ol, 3-(3',4'-Dichlorophenyl)-2-ethylpropan-1-ol, 2-Ethyl-3-(2'-methylphenyl)-propan-1-ol, 2-Ethyl-3-(4'-methylphenyl)-propan-1-ol, 3-(3',4'-Dimethylphenyl)-2-ethylpropan-1-ol, 2-Ethyl-3-(4'-methoxyphenyl)-propan-1-ol, 3-(3',4'-Dimethoxyphenyl)-2-ethylpropan-1-ol, 2-Allyl-3-phenylpropan-1-ol and 2-n-Pentyl-3-phenylpropan-1-ol.

Complexing substance may also support the deodorizing effect by forming stable complexes with heavy metal ions (e.g., iron or copper) that have an oxidatively catalytic action. Suitable complexing substances are for example the salts of ethylenediamine tetraacetic acid or of nitrilotriacetic acid and the salts of 1-Hydroxyethane-1,2-diphosphonic acid.

In a further, particularly preferred embodiment, the compositions as contemplated herein may contain at least one antiperspirant agent and also at least one deodorant agent.

The packaging of the compositions as contemplated herein, which are applied as a spray, is preferably adapted to the requirements of the desired spray application.

The compositions as contemplated herein are present in suspension, in other words the sweat suppressing agent and optionally other insoluble components are suspended in a liquid or solid carrier. Liquid-dispersed systems of this kind, e.g., dispersions which are to be applied as roll-ons or as a spray, should be shaken before use.

Preferred compositions as contemplated herein may be packaged e.g., in pump or squeeze dispensers, particularly in multichamber pump or squeeze dispensers. Dispensers of such kind use air, particularly ambient air, as the propellant and/or transport the composition as contemplated herein by pump action.

In a further preferred embodiment of the present disclosure, the composition is applied by employing a compressed or liquefied propellants. For this purpose, the composition as contemplated herein is packaged in a spray container together with a propellant. In this context, the propellant and the composition as contemplated herein may exist as a mixture. However, it is also possible for the propellant and the composition as contemplated herein to be separated from each other, e.g., in "bag-in-can" spray containers.

Unless otherwise specified, all quantities indicated refer to the weight of the composition without the propellant.

The packaging in a multichamber dispenser offers particular technical advantages.

The multichamber dispenser may also be used in such manner that one chamber is filled with the composition as contemplated herein while the other chamber contains the compressed propellant. One multichamber dispenser of such kind is for example a "bag-in-can" package.

However, both chambers may also communicate with each other in such manner that the composition as contemplated herein is separated into two part compositions, which may be expelled from the packaging simultaneously, for example from separate apertures or from a single aperture.

Further preferred compositions as contemplated herein are exemplified in that that are packaged with at least one propellant in a suitable pressurized container.

Propellants (propellant gases) that are preferred as contemplated herein are selected from propane, propene, n-Butane, iso-butane, iso-butene, n-Pentane, pentene, iso-Pentane, iso-Pentene, methane, ethane, dimethylether, nitrogen, air, oxygen, nitrous oxide, dichlorofluoromethane, chlorodifluoromethane, chlorofluoromethane, 1,2,2,2-Tetrachloro-1-fluoroethane, 1,2,2,2-Tetrachloro-2-fluoroethane, 1,2,2-Trichloro-1,2-difluoroethane, 1,2,2-Trichloro-1.2-difluoroethane, 1,2,2-Trichloro-2.2-difluoroethane, 2,2-Dichloro-1,2,2-trifluoroethane, 1,2-Dichloro-1,2,2-trifluoroethane, 2-Chloro-1,2,2,2-tetrafluoroethane, 1-Chloro-1,2,2,2-tetrafluoroethane, 1,2,2-Trichloro-2-fluoroethane, 1,2-Dichloro-1,2-difluoroethane, 1,2-Dichloro-1,2-difluoroethane, 1-Chloro-1,2,2-trifluoroethane, 2-Chloro-1,2,2-trifluoroethane, 1,2-Dichloro-1-fluoroethane, 1,2-Dichloro-1-fluoroethane, 2-Chloro-1,2-difluoroethane, 1-Chloro-1,2-difluoroethane, 1-Chloro-2-fluoroethane, 1-Chloro-1-fluoroethane, 2-Chloro-1,2-difluoroethenr, 1,2,2,3-Tetrafluoroethane, heptafluoro-n-propane, perfluoroethane, monochlorodifluoromethane, 1,2-Difluoroethane, either individually or in combination.

Particularly preferred are propane, n-Butane, iso-Butane and particularly preferably mixtures of these propellants. Also preferred are 1,2-Difluoroethane, Propane, n-Butane, iso-Butane and mixtures of these propellants, particularly mixtures of 1,2-Difluoroethane and n-Butane.

Hydrophilic propellant gases such as carbon dioxide, may also be used within the meaning of the present disclosure if the proportion of hydrophilic gases is low and a lipophilic propellant gas (e.g., propane/butane) is the predominant component. Particularly preferred are propane, n-Butane, iso-Butane and mixtures of these propellant gases. It has been found that the use of n-Butane as the sole propellant gas can be particularly preferable as contemplated herein.

The propellant is present in a quantity of preferably from about 10 to about 95% w/w, particularly preferably from about 30 to about 90% w/w and most particularly preferably from about 60 to about 86% w/w, and still more particularly preferably from about 70, about 72, about 74, about 76, about 78, about 82, about 84 or about 85% w/w of the total weight of the respective preparation including the composition as contemplated herein (suspension) and the propellant.

Receptacles of metal (aluminum, tin sheet, tin), of protected or non-splintering plastic or of glass coated on the outside with plastic, may be considered for use as compressed gas containers, wherein the selection will also be made taking into account such factors as resistance to pressure and breakage, corrosion resistance, ease of filling and visual appearance, ease of handling, ease of printing etc. Special interior protection coatings ensure resistance to corrosion by the suspension as contemplated herein. A preferred interior protection coating as contemplated herein is an epoxy-phenol varnish which is available under the trade name Hoba 7407 P among others. Particularly preferably, the values used also have a valve plate which is coated on the inside, wherein the coating and the valve material are compatible with each other. If aluminum valves are used, the valve plates thereof may be coated on the inside for example with Micoflex lacquer. If tin sheet valves are used as contemplated herein, the valve plates thereof may be coated on the inside e.g. with PET (polyethylene terephthalate).

The containers may be equipped with a suitable spray head. Expulsion rates from about 0.2 g/s to about 2.0 g/s relative to the full containers are possible depending on the spray head used.

Compositions as contemplated herein which may be sprayed as a spray preferably contain at least one thickening agent which is selected from hydrophobically modified clay minerals.

Hydrophobically modified clay minerals are understood to be clay minerals in which the naturally present metal cations have been partly or completely replaced with cations having substituted hydrophobic groups, preferably ammonium cations substituted with long-chain alkyl groups, wherein the long-chain alkyl groups contain preferably from about 5 to about 30, particularly preferably from about 7 to about 25, most particularly preferably from about 10 to about 20 carbon atoms and are straight, branched or cyclic.

Preferred hydrophobically modified clay minerals are selected from hydrophobically modified montmorillonites, hydrophobically modified hectorites and hydrophobically modified bentonites, particularly preferably from disteardimonium hectorite, stearalkonium hectorite, Quaternium-18 Hectorite and Quaternium-18 Bentonite. Preferred compositions as contemplated herein are exemplified in that that contain at least one hydrophobized clay mineral in a total quantity from about 0.5 to about 10% w/w, preferably from about 1 to about 7% w/w, particularly preferably from about 2 to about 6% w/w, most particularly preferably from about 2.5 to about 4% w/w, relative to the total weight of the respective propellant free composition as contemplated herein. Further lipophilic thickening agent that are preferred as contemplated herein are selected from pyrogenic silicas, e.g., the commercial products of the Aerosil® line by Evonik. Particularly preferred as hydrophobized pyrogenic silicas, particularly preferably silica silylate and silica dimethyl silylate. Compositions that are preferred as contemplated herein are exemplified in that they contain at least one pyrogenic silica, preferably at least one hydrophobically modified pyrogenic silica, in a total quantity from about 0.5 to about 10% w/w, preferably from about 0.8 to about 5% w/w, particularly preferably from about 1 to about 4% w/w, most particularly preferably from about 1.5 to about 2% w/w, relative to the total weight of the respective propellant free composition as contemplated herein. Further preferred compositions as contemplated herein are exemplified in that they contain at least at least one hydrophobically modified pyrogenic silica and at least one hydrophilic silica.

A further object of the present disclosure is a non-therapeutic, cosmetic method for reducing and/or regulating sweat production and/or body odor, in which a composition as contemplated herein is applied in an effective quantity to the skin, preferably to the skin in the region of the armpits.

The description of the compositions as contemplated herein applies equally mutatis mutandis with regard to preferred embodiments thereof.

A further object of the present disclosure is the use of rice starch and cornstarch or maize amylopectin in sweat suppressing compositions, containing at least one sweat suppressing agent which is present in suspended, undissolved form and is selected from aluminum salts and aluminum-zirconium salts, preferably to improve the skin feel while at the same time minimizing the white residues on items of clothing after use of the sweat suppressing composition, wherein the sweat suppressing composition is particularly preferably a composition as contemplated herein.

The description of the compositions as contemplated herein applies equally mutatis mutandis with regard to preferred embodiments thereof.

A further object of the present disclosure is a sprayable antiperspirant containing a composition as contemplated herein, exemplified in that the composition as contemplated herein is present in an aerosol container together with a compressed, gas-phase propellant.

The description of the compositions as contemplated herein applies equally mutatis mutandis with regard to preferred embodiments thereof.

EXAMPLES

In order to produce the antiperspirant suspensions, the ingredients (see Table) were mixed and homogenized at 30° C. The formulations were introduced into aerosol containers in a weight ratio of 3:17 with the propellant propane/butane (15/85). The aerosols were sprayed onto black cardboard for 2 seconds, and the white residue evaluated by comparison with the reference scale (0=no white residue, 4=very pronounced white residue). The skin feel was evaluated directly by two trained experts. (1=very dry, 5=very oily/greasy)

Table 1 shows examples of 5 comparison formulations V1, V2, V3, V4 and V5, and a formulation E1 as contemplated herein, and the evaluation of the residue formation and skin feel. Table 2 shows three further examples E2, E3 and E4 of further formulations as contemplated herein. These examples are not limiting of the present disclosure. Upon consideration of V1, it may be seen that in the absence of the starch components and non-volatile oils, while a good skin feel is obtained there is also a pronounced white residue left behind. Example V5 shows that with a large quantity of rice starch the skin feel is also good, but in this case too a white residue remains, originating from the starch. Examples V2, V3 and V4 indicate that small quantities of the individual starch components do not a skin fell that is sufficiently comfortable for the consumer. Only when small quantities of both starch components (octenyl succinate of a hydrogenated cornstarch with rice starch) are combined with non-volatile oils is both a good skin feel perceived and low white residue visible.

TABLE 1

Examples of 5 comparison formulations V1, V2, V3, V4 and V5 and a formulation E1 as contemplated herein, with the evaluation of residue formation and skin feel.

| | V1 % w/w | V2 % w/w | V3 % w/w | V4 % w/w | V5 % w/w | E1 % w/w |
|---|---|---|---|---|---|---|
| Octenyl succinate of a hydrogenated cornstarch | — | — | 2.0 | — | — | 1.0 |
| Rice starch | — | — | — | 2.0 | 10.0 | 1.0 |
| Cyclopentasiloxane | 73.0 | 21.0 | 21.0 | 21.0 | 12.0 | 21.0 |
| Isopropyl myristate | — | 30.0 | 30.0 | 30.0 | 30.0 | 30.0 |
| Ethylhexyl palmitate | — | 6.0 | 6.0 | 6.0 | 6.0 | 6.0 |
| Dimethicone 5 cSt | — | 10.0 | 10.0 | 10.0 | 10.0 | 10.0 |
| Disteardimonium hectorite | 2.5 | 2.5 | 2.5 | 2.5 | 2.5 | 2.5 |
| Propylene carbonate | 1.0 | 1.0 | 1.0 | 1.0 | 1.0 | 1.0 |
| Aluminum chlorohydrate | 23.5 | 23.5 | 23.5 | 23.5 | 23.5 | 23.5 |
| White residue | 4 | 2 | 2 | 2 | 4 | 2 |
| Skin feel | 1 | 4 | 3-4 | 3-4 | 2 | 2 |

TABLE 2

Three examples E2, E3 and E4 of formulations as contemplated herein

| | E2 % w/w | E3 % w/w | E4 % w/w |
|---|---|---|---|
| Cyclopentasiloxane (Xiameter 0245 fluid) | 21.0 | 20.0 | 21.0 |
| Isopropyl palmitate (BASF) | 30.0 | 30.0 | 30.0 |
| Ethylhexyl palmitate (Cegesoft C24, BASF) | 6.0 | 6.0 | 6.0 |
| Octenyl succinate of a hydrogenated cornstarch (Capsul ENC, AkzoNobel) | 0.5 | 1.5 | 0.7 |
| Rice starch (Rice starch D.S.A. 7, Agrana AG) | 0.5 | 0.9 | 0.3 |
| Dimethicone (Xiameter PMX-200 Fluid 5CS) | 10.0 | 10.0 | 10.0 |
| Disteardimonium hectorite (Bentone 38 V CG) | 2.5 | 2.5 | 2.5 |
| Propylene carbonate | 1.0 | 1.0 | 1.0 |
| Aluminum chlorohydrate (AACH 7172, SummitReheis) | 23.5 | 23.5 | 23.5 |
| Fragrance | 5.0 | 5.0 | 5.0 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. Antiperspirant composition for personal body care, comprising
   a) at least one sweat suppressing agent which is present in suspended, non-dissolved form and is selected from aluminum salts and aluminum-zirconium salts,
   b) from about 0 to about 7% w/w free water,
   c) at least one non-volatile oil that is liquid at a temperature of about 20° C. and a pressure of about 1013.25 mbar in a total quantity from about 28 to about 61% w/w,
   d) at least one volatile oil that is liquid at a temperature of about 20° C. and a pressure of about 1013.25 mbar in a total quantity from about 5 to about 35% w/w,
   e) rice starch, and
   f) cornstarch,
   wherein all percentages by weight relate to the weight of the composition, disregarding any propellants present,
   wherein the at least one volatile oil is selected from volatile silicone oils and volatile non-silicone oils and mixtures thereof;
   wherein the rice starch is present in an amount of from about 0.3 to about 1% w/w,
   wherein the cornstarch is esterified with 1-octadecenyl succinic acid and is present in an amount of from about 0.4 to about 1.5% w/w, wherein all percentages by weight relate to the weight of the composition, disregarding any propellants present,
   wherein the at least one volatile silicone oil comprises decamethylcyclopentasiloxane,
   wherein the at least one non-volatile oil is chosen from dimethicone, isopropyl myristate, 2-ethylhexyl palmitate, isopropyl palmitate, and combinations thereof,
   wherein at least one sweat suppressing agent is included in a total quantity from about 23 to about 27% w/w, relative to the total weight of the active substance without water of crystallization (United States Pharmacopoeia (USP)) in the composition disregarding any propellants present, and
   wherein the composition further comprises disteardimonium hectorite and propylene carbonate.

2. Composition according to claim 1, wherein the rice starch is present as a powder treated with cationic surfactants, wherein the percentage of cationic surfactants is from about 0.01 to about 0.3% w/w relative to the weight of the rice starch.

3. Composition according to claim 1, wherein the cornstarch is included in the form of a capsule materials for active agents.

4. Composition according to claim 1, wherein the at least one volatile silicone oil further comprises octamethyl cyclotetrasiloxane, dodecamethyl cyclohexasiloxane, hexamethyl disiloxane, octamethyl trisiloxane and decamethyl tetrasiloxane and mixtures thereof.

5. Composition according to claim 1, wherein the at least one non-volatile oil further comprises esters of linear or branched saturated or unsaturated fatty alcohols having from about 2 to about 30 carbon atoms with linear or branched saturated or unsaturated fatty acids having from about 2 to about 30 carbon atoms, which is optionally hydroxylated.

6. Composition according to claim 1, wherein the at least one non-volatile oil further comprises non-volatile silicone oils.

7. Composition according to claim 1, wherein at least one thickening agent, selected from hydrophobized clay minerals, is included in a total quantity from about 0.5 to about 10% w/w, relative to the total weight of the composition without propellant.

8. The composition of claim 1 wherein the cornstarch is present in the form of one or more capsules wherein each capsule comprises one or more active agents chosen from fragrances, perfume oils, skin cooling agents, vitamins and/or antioxidants or combinations thereof.

9. The composition of claim 1 wherein the at least one volatile non-silicone oil further comprises isodecane, isoundecane, isododecane, isotridecane, isotetradecane, isopentadecane, and isohexadecane, and mixtures thereof.

10. The composition of claim 1 wherein the
at least one sweat suppressing agent is present in an amount of about 23.5% w/w;
rice starch is present in an amount of about 1% w/w,
the cornstarch that is esterified with 1-octadecenyl succinic acid is present in an amount of about 1% w/w, wherein all percentages by weight relate to the weight of the composition in each case, disregarding any propellants present,
the decamethylcyclopentasiloxane is present in an amount of about 21% w/w;
the isopropyl myristate is present in an amount of about 30% w/w; and
the 2-ethylhexy palmitate is present in an amount of about 6% w/w.

11. The composition of claim 1 wherein the
at least one sweat suppressing agent is present in an amount of about 23.5% w/w;
rice starch is present in an amount of about 0.5% w/w,
the cornstarch that is esterified with 1-octadecenyl succinic acid is present in an amount of about 0.5% w/w, wherein all percentages by weight relate to the weight of the composition in each case, disregarding any propellants present,
the decamethylcyclopentasiloxane is present in an amount of about 21% w/w;
the isopropyl palmitate is present in an amount of about 30% w/w; and
the 2-ethylhexy palmitate is present in an amount of about 6% w/w.

12. The composition of claim 1 wherein the
at least one sweat suppressing agent is present in an amount of about 23.5% w/w;
rice starch is present in an amount of about 0.9% w/w,
the cornstarch that is esterified with 1-octadecenyl succinic acid is present in an amount of about 1.5% w/w, wherein all percentages by weight relate to the weight of the composition in each case, disregarding any propellants present,
the decamethylcyclopentasiloxane is present in an amount of about 20% w/w;
the isopropyl palmitate is present in an amount of about 30% w/w; and
the 2-ethylhexy palmitate is present in an amount of about 6% w/w.

13. The composition of claim 1 wherein the
at least one sweat suppressing agent is present in an amount of about 23.5% w/w;
rice starch is present in an amount of about 0.3% w/w,
the cornstarch that is esterified with 1-octadecenyl succinic acid is present in an amount of about 0.7% w/w, wherein all percentages by weight relate to the weight of the composition in each case, disregarding any propellants present,
the decamethylcyclopentasiloxane is present in an amount of about 21% w/w;
the isopropyl palmitate is present in an amount of about 30% w/w; and
the 2-ethylhexy palmitate is present in an amount of about 6% w/w.

14. The composition of claim 1 having about 0% w/w of free water.

15. A non-therapeutic, cosmetic method for reducing and/or regulating sweat production and/or body odor of a subject, in which a composition according to claim 1 is applied in an effective quantity to the skin of the subject.

16. Sprayable antiperspirant comprising a composition according to claim 1, wherein the composition is present in an aerosol container together with a compressed, gas-phase propellant.

* * * * *